(12) United States Patent
Parikh et al.

(10) Patent No.: US 6,979,456 B1
(45) Date of Patent: Dec. 27, 2005

(54) ANTICANCER COMPOSITIONS

(75) Inventors: Indu Parikh, Chapel Hill, NC (US); Iskandar Moussa, Beirut (LB); Alain Carrier, Quebec (CA)

(73) Assignee: Jagotec AG, Muttenz (CH)

( * ) Notice: Subject to any disclaimer, the term of this patent is extended or adjusted under 35 U.S.C. 154(b) by 0 days.

(21) Appl. No.: 09/281,430

(22) Filed: Mar. 30, 1999

Related U.S. Application Data

(60) Provisional application No. 60/080,273, filed on Apr. 1, 1998, provisional application No. 60/080,272, filed on Apr. 1, 1998.

(51) Int. Cl.[7] .......................... A61F 2/02; A61K 9/127; A61K 9/66
(52) U.S. Cl. ...................... 424/422; 424/450; 424/455; 514/937; 514/938
(58) Field of Search .............................. 424/422, 450, 424/455; 514/937, 938

(56) References Cited

U.S. PATENT DOCUMENTS

| | | | |
|---|---|---|---|
| 2,803,582 A | 8/1957 | Cherney |
| 3,137,631 A | 6/1964 | Soloway |
| 3,594,476 A | 7/1971 | Merrill |
| 3,715,432 A | 2/1973 | Merrill |
| 3,755,557 A | 8/1973 | Jacobs |
| 3,937,668 A | 2/1976 | Zolle |
| 3,960,757 A | 6/1976 | Morishita et al. |
| 4,053,585 A | 10/1977 | Allison et al. |
| 4,056,635 A | 11/1977 | Glen et al. |
| 4,073,943 A | 2/1978 | Wretlind et al. |
| 4,078,052 A | 3/1978 | Papahadjopoulos |
| 4,089,801 A | 5/1978 | Schneider |
| 4,102,806 A | 7/1978 | Kondo et al. |
| 4,107,288 A | 8/1978 | Oppenheim et al. |
| 4,133,874 A | 1/1979 | Miller et al. |
| 4,145,410 A | 3/1979 | Sears |
| 4,147,767 A | 4/1979 | Yapel, Jr. |
| 4,168,308 A | 9/1979 | Wretlind et al. |
| 4,235,871 A | 11/1980 | Papahadjopoulos et al. |
| 4,241,046 A | 12/1980 | Papahadjopoulos et al. |
| 4,271,196 A | 6/1981 | Schmidt |
| 4,298,594 A | 11/1981 | Sears et al. |
| 4,302,459 A | 11/1981 | Steck et al. |
| 4,308,166 A | 12/1981 | Marchetti et al. |
| 4,309,421 A | 1/1982 | Ghyczy et al. |
| 4,316,884 A | 2/1982 | Alam et al. |
| 4,320,121 A | 3/1982 | Sears |
| 4,328,222 A | 5/1982 | Schmidt |
| 4,329,332 A | 5/1982 | Couvreur et al. |
| 4,331,654 A | 5/1982 | Morris |
| 4,332,795 A | 6/1982 | Ghyczy et al. |

(Continued)

FOREIGN PATENT DOCUMENTS

CH          688 504 A5    3/1997

(Continued)

OTHER PUBLICATIONS

Lundberg, B. A submicron lipid emulsion coated with amphipathic polyethylene gllycol for parenteral administration of paclitaxel J. Pharm. Pharmacol 49(1):16-21, Jan. 1997.*

(Continued)

*Primary Examiner*—Carlos A. Azpuru
(74) *Attorney, Agent, or Firm*—Mintz, Levin, Cohn, Ferris, Glovsky and Popeo, P.C.; Daniel F. Coughlin, Esq.; Nicholas P. Triano, III, Esq.

(57) ABSTRACT

Pharmaceutical dosage forms for anticancer drugs, and paclitaxel in particular, are described in which the active drug is formulated as storage stable self-emulsifying pre-concentrate.

52 Claims, 1 Drawing Sheet

U.S. PATENT DOCUMENTS

Figure 1:
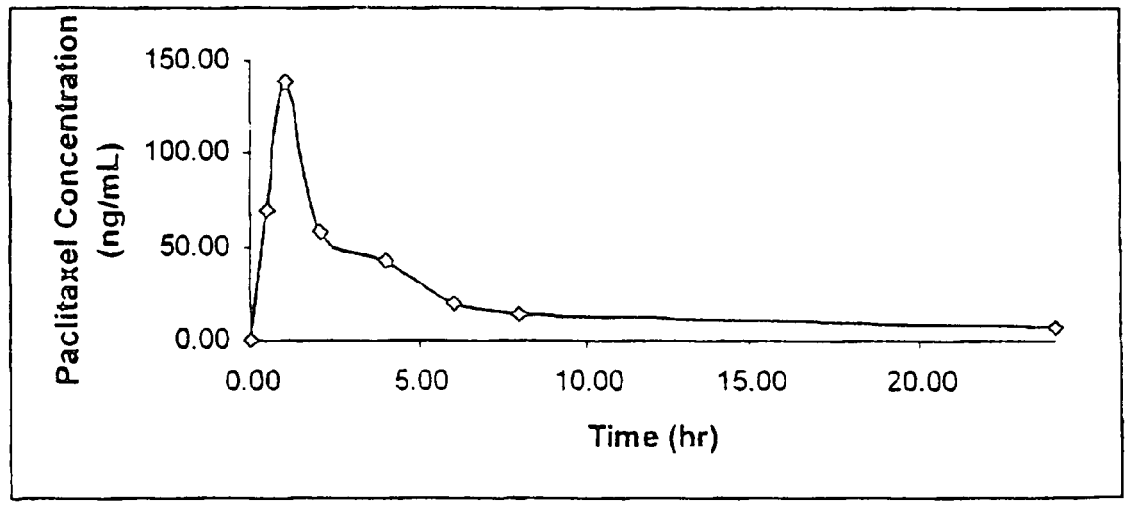

| | | | |
|---|---|---|---|
| 4,332,796 A | 6/1982 | Los | |
| 4,340,594 A | 7/1982 | Mizushima et al. | |
| 4,345,588 A | 8/1982 | Widder et al. | |
| 4,351,831 A | 9/1982 | Growdon et al. | |
| 4,356,167 A | 10/1982 | Kelly | |
| 4,369,182 A | 1/1983 | Ghyczy et al. | |
| 4,371,516 A | 2/1983 | Gregory et al. | |
| 4,378,354 A | 3/1983 | Ghyczy et al. | |
| 4,394,372 A | 7/1983 | Taylor | |
| 4,397,846 A | 8/1983 | Weiner et al. | |
| 4,411,894 A | 10/1983 | Schrank et al. | |
| 4,411,933 A | 10/1983 | Samejima et al. | |
| 4,421,747 A | 12/1983 | Ghyczy et al. | |
| 4,427,649 A | 1/1984 | Dingle et al. | |
| 4,432,975 A | 2/1984 | Libby | |
| 4,448,765 A | 5/1984 | Ash et al. | |
| 4,452,817 A | 6/1984 | Glen et al. | |
| 4,483,847 A | 11/1984 | Augart | |
| 4,485,054 A | 11/1984 | Mezei et al. | |
| 4,492,720 A | 1/1985 | Mosier | |
| 4,515,736 A | 5/1985 | Deamer | |
| 4,522,803 A | 6/1985 | Lenk et al. | |
| 4,610,868 A | 9/1986 | Fountain et al. | |
| 4,613,505 A | 9/1986 | Mizushima et al. | |
| 4,622,219 A | 11/1986 | Haynes | |
| 4,629,626 A | 12/1986 | Miyata et al. | |
| RE32,393 E | 4/1987 | Wretlind et al. | |
| 4,675,236 A | 6/1987 | Ohkawara et al. | |
| 4,687,762 A | 8/1987 | Fukushima et al. | |
| 4,711,902 A | 12/1987 | Serno | |
| 4,719,239 A | 1/1988 | Muller et al. | |
| 4,725,422 A | 2/1988 | Miyabayashi et al. | |
| 4,756,910 A | 7/1988 | Yagi et al. | |
| 4,758,598 A | 7/1988 | Gregory | |
| 4,762,720 A | 8/1988 | Jizomoto | |
| 4,766,046 A | 8/1988 | Abra et al. | |
| 4,776,991 A | 10/1988 | Farmer et al. | |
| 4,798,846 A | 1/1989 | Glen et al. | |
| 4,798,860 A | 1/1989 | Parr | |
| 4,800,079 A | 1/1989 | Boyer | |
| 4,801,455 A | 1/1989 | List et al. | |
| 4,803,070 A | 2/1989 | Cantrell et al. | |
| 4,806,350 A | 2/1989 | Gerber | |
| 4,806,352 A | 2/1989 | Cantrell | |
| 4,826,687 A | 5/1989 | Nerome et al. | |
| 4,839,111 A | 6/1989 | Huang | |
| 4,880,634 A | 11/1989 | Speiser | |
| 4,895,726 A | 1/1990 | Curtet et al. | |
| 4,961,890 A | 10/1990 | Boyer | |
| 4,963,367 A | 10/1990 | Ecanow | |
| 4,970,076 A | 11/1990 | Horrobin | |
| 4,973,465 A | 11/1990 | Baurain et al. | |
| 4,990,337 A | 2/1991 | Kurihara et al. | |
| 5,030,453 A | 7/1991 | Lenk et al. | |
| 5,091,187 A | 2/1992 | Haynes | |
| 5,091,188 A | 2/1992 | Haynes | |
| 5,098,606 A | 3/1992 | Nakajima et al. | |
| 5,100,591 A | 3/1992 | Leclef et al. | |
| 5,128,147 A | 7/1992 | Leveen et al. | |
| 5,145,684 A | 9/1992 | Liversidge et al. | |
| 5,152,923 A | 10/1992 | Weder et al. | |
| 5,164,380 A | 11/1992 | Carli et al. | |
| 5,167,950 A | 12/1992 | Lins | |
| 5,169,847 A | 12/1992 | Nagy nee Kriesfalussy et al. | |
| 5,178,878 A | 1/1993 | Wehling et al. | |
| 5,179,079 A | 1/1993 | Hansen et al. | |
| 5,217,707 A | 6/1993 | Szabo et al. | |
| 5,246,707 A | 9/1993 | Haynes | |
| 5,256,422 A | 10/1993 | Albert et al. | |
| 5,269,979 A | 12/1993 | Fountain | |
| 5,272,137 A | 12/1993 | Blase et al. | |
| 5,298,262 A | 3/1994 | Na et al. | |
| 5,302,401 A | 4/1994 | Liversidge et al. | |
| 5,304,564 A | 4/1994 | Tsuboi et al. | |
| 5,314,915 A | 5/1994 | Rencher | |
| 5,326,552 A | 7/1994 | Na et al. | |
| 5,336,507 A | 8/1994 | Na et al. | |
| 5,338,761 A | 8/1994 | Nakajima et al. | |
| 5,340,564 A | 8/1994 | Illig et al. | |
| 5,342,625 A * | 8/1994 | Hauser et al. | 424/455 |
| 5,346,702 A | 9/1994 | Na et al. | |
| 5,352,459 A | 10/1994 | Hollister et al. | |
| 5,360,593 A | 11/1994 | Bapatla | |
| 5,364,632 A | 11/1994 | Benita et al. | |
| 5,364,633 A | 11/1994 | Hill et al. | |
| 5,389,377 A | 2/1995 | Chagnon et al. | |
| 5,399,363 A | 3/1995 | Liversidge et al. | |
| 5,407,683 A * | 4/1995 | Shively | 424/439 |
| 5,437,055 A | 7/1995 | Wheatley, III | |
| 5,439,055 A | 8/1995 | Card et al. | |
| 5,447,710 A | 9/1995 | Na et al. | |
| 5,470,583 A | 11/1995 | Na et al. | |
| 5,473,055 A | 12/1995 | Mongelli et al. | 530/329 |
| 5,478,860 A | 12/1995 | Wheeler et al. | 514/449 |
| 5,496,818 A | 3/1996 | Schaupp et al. | |
| 5,498,420 A | 3/1996 | Mentrup et al. | |
| 5,498,421 A | 3/1996 | Grinstaff et al. | |
| 5,510,118 A | 4/1996 | Bosch et al. | |
| 5,518,730 A | 5/1996 | Fuisz | |
| 5,527,537 A | 6/1996 | Dietl | |
| 5,529,785 A | 6/1996 | Dietl | |
| 5,545,628 A | 8/1996 | Deboeck et al. | |
| RE35,338 E | 9/1996 | Haynes | |
| 5,552,160 A | 9/1996 | Liversidge et al. | |
| 5,560,931 A | 10/1996 | Eickhoff et al. | 424/489 |
| 5,569,448 A | 10/1996 | Wong et al. | |
| 5,569,464 A | 10/1996 | Endo et al. | |
| 5,571,536 A | 11/1996 | Eickhoff et al. | |
| 5,576,016 A | 11/1996 | Amselem et al. | |
| 5,578,325 A | 11/1996 | Domb et al. | |
| 5,589,455 A | 12/1996 | Woo | |
| 5,589,508 A | 12/1996 | Schlotzer et al. | |
| 5,603,951 A | 2/1997 | Woo | |
| 5,607,694 A | 3/1997 | Marx | |
| 5,616,330 A | 4/1997 | Kaufman et al. | 424/400 |
| 5,618,522 A | 4/1997 | Kaleta et al. | |
| 5,631,019 A | 5/1997 | Marx | |
| 5,631,023 A | 5/1997 | Kearney et al. | |
| 5,637,625 A | 6/1997 | Haynes | |
| 5,639,474 A | 6/1997 | Woo | |
| 5,639,724 A | 6/1997 | Cavanak | |
| 5,645,856 A | 7/1997 | Lacy et al. | 424/455 |
| 5,648,375 A | 7/1997 | Abraham | |
| 5,651,982 A | 7/1997 | Marx | |
| 5,651,991 A | 7/1997 | Sugiyama et al. | |
| 5,652,212 A | 7/1997 | Cavanak et al. | |
| 5,656,286 A | 8/1997 | Miranda et al. | |
| 5,660,837 A | 8/1997 | Lundquist | |
| 5,660,854 A | 8/1997 | Haynes et al. | |
| 5,660,858 A | 8/1997 | Parikh et al. | |
| 5,662,932 A | 9/1997 | Amselem et al. | |
| 5,663,198 A | 9/1997 | Reul et al. | |
| 5,665,700 A | 9/1997 | Cho et al. | |
| 5,676,928 A | 10/1997 | Klaveness et al. | |
| 5,677,341 A | 10/1997 | Lyons | |
| 5,681,846 A | 10/1997 | Trissel | 514/449 |
| 5,686,102 A | 11/1997 | Gross et al. | |
| 5,688,528 A | 11/1997 | Carlsson et al. | |
| 5,693,337 A | 12/1997 | Suzuki et al. | |
| 5,696,153 A | 12/1997 | Ainsworth et al. | |
| 5,714,520 A | 2/1998 | Jones et al. | |
| 5,719,197 A | 2/1998 | Kanios et al. | |
| 5,731,355 A | 3/1998 | Jones et al. | |
| 5,731,356 A | 3/1998 | Jones et al. | |

| | | |
|---|---|---|
| 5,733,572 A | 3/1998 | Unger et al. |
| 5,750,142 A | 5/1998 | Friedman et al. |
| 5,770,222 A | 6/1998 | Unger et al. |
| 5,773,026 A | 6/1998 | Schlipalius |
| 5,776,491 A | 7/1998 | Allen, Jr. et al. |
| 5,776,495 A | 7/1998 | Duclos et al. |
| 5,827,536 A | 10/1998 | Laruelle |
| 5,827,822 A | 10/1998 | Floc'h et al. |
| 5,834,025 A | 11/1998 | de Garavilla et al. |
| 5,843,465 A | 12/1998 | Lundquist |
| 5,851,275 A | 12/1998 | Amidon et al. |
| 5,853,755 A | 12/1998 | Foldvari |
| 5,858,398 A | 1/1999 | Cho |
| 5,858,410 A | 1/1999 | Muller et al. |
| 5,880,148 A | 3/1999 | Edgar et al. |
| 5,885,597 A | 3/1999 | Botknecht et al. |
| 5,908,869 A | 6/1999 | Jones et al. |
| 5,912,007 A | 6/1999 | Pan et al. |
| 5,912,271 A | 6/1999 | Brodin et al. |
| 5,916,596 A | 6/1999 | Desai et al. |
| 5,922,355 A | 7/1999 | Parikh et al. |
| 5,929,030 A * | 7/1999 | Hamied et al. ............... 514/9 |
| 5,932,243 A | 8/1999 | Fricker et al. |
| 5,958,379 A | 9/1999 | Regenold et al. |
| 5,962,536 A | 10/1999 | Komer |
| 5,965,160 A * | 10/1999 | Benita et al. ............... 424/455 |
| 5,968,987 A * | 10/1999 | Charman et al. ........... 514/656 |
| 5,972,366 A | 10/1999 | Haynes et al. |
| 5,976,577 A | 11/1999 | Green et al. |
| 5,994,318 A | 11/1999 | Gould-Fogerite et al. |
| 6,004,573 A * | 12/1999 | Rathi et al. ................. 424/426 |
| 6,013,665 A | 1/2000 | DeMichele et al. |
| 6,017,513 A | 1/2000 | Betbeder et al. |
| 6,019,997 A | 2/2000 | Scholz et al. |
| 6,022,547 A | 2/2000 | Herb et al. |
| 6,028,108 A | 2/2000 | George |
| 6,031,007 A | 2/2000 | Brodin et al. |
| 6,045,829 A | 4/2000 | Liversidge et al. |
| 6,046,163 A | 4/2000 | Stuchlik et al. |
| 6,057,289 A | 5/2000 | Mulye |
| 6,063,762 A | 5/2000 | Hong et al. |
| 6,071,927 A | 6/2000 | Baker et al. |
| 6,071,928 A | 6/2000 | Curtis et al. |
| 6,075,059 A | 6/2000 | Reader |
| 6,086,376 A | 7/2000 | Moussa et al. |
| 6,096,338 A | 8/2000 | Lacy et al. |
| 6,100,302 A | 8/2000 | Pejaver et al. |
| 6,113,921 A | 9/2000 | Friedman et al. |
| 6,120,797 A | 9/2000 | Meers et al. |
| 6,121,261 A | 9/2000 | Glatt et al. |
| 6,140,373 A | 10/2000 | May et al. |
| 6,140,374 A | 10/2000 | May et al. |
| 6,147,122 A | 11/2000 | Mirejovsky et al. |
| 6,150,423 A | 11/2000 | Carpenter |
| 6,153,217 A | 11/2000 | Jin et al. |
| 6,160,007 A | 12/2000 | DeMichele et al. |
| 6,177,477 B1 | 1/2001 | George et al. |
| 6,180,136 B1 | 1/2001 | Larson et al. |
| 6,190,894 B1 | 2/2001 | Thornfeldt et al. |
| 6,197,323 B1 | 3/2001 | Georgieff |
| 6,204,257 B1 | 3/2001 | Stella et al. |
| 6,217,886 B1 | 4/2001 | Onyüuksel et al. |
| 6,221,383 B1 | 4/2001 | Miranda et al. |
| 6,228,399 B1 | 5/2001 | Parikh et al. |
| 6,232,311 B1 | 5/2001 | Rubniak et al. |
| 6,242,446 B1 | 6/2001 | Glatt et al. |
| 6,254,853 B1 | 7/2001 | Hendler et al. |
| 6,261,537 B1 | 7/2001 | Klaveness et al. |
| 6,264,917 B1 | 7/2001 | Klaveness et al. |
| 6,264,981 B1 | 7/2001 | Zhang et al. |
| 6,267,985 B1 | 7/2001 | Liversidge et al. |
| 6,267,989 B1 | 7/2001 | Liversidge et al. |
| 6,270,806 B1 | 8/2001 | Liversidge et al. |
| 6,274,633 B1 | 8/2001 | Franks et al. |
| 6,281,175 B1 | 8/2001 | Lyons et al. |
| 6,284,268 B1 | 9/2001 | Mishra et al. |
| 6,288,040 B1 | 9/2001 | Müller et al. |
| 6,288,127 B1 | 9/2001 | Bienlarz et al. |
| 6,294,191 B1 | 9/2001 | Meers et al. |
| 6,294,192 B1 | 9/2001 | Patel et al. |
| 6,297,985 B1 | 10/2001 | Kang |
| 6,309,623 B1 | 10/2001 | Weers et al. |
| 6,312,715 B1 | 11/2001 | Cantor et al. |
| 6,326,406 B1 | 12/2001 | De Tommaso |
| 6,328,708 B1 | 12/2001 | Georgleff |
| 6,331,289 B1 | 12/2001 | Klaveness et al. |
| 6,332,138 B1 | 12/2001 | Hull et al. |
| 6,337,092 B1 | 1/2002 | Khan et al. |
| 6,350,480 B1 | 2/2002 | Urnezis et al. |
| 6,387,409 B1 | 5/2002 | Khan et al. |
| 6,391,336 B1 | 5/2002 | Royer |
| 6,391,832 B2 | 5/2002 | Lyons et al. |
| 6,399,087 B1 | 6/2002 | Zhang et al. |
| 6,410,583 B1 | 6/2002 | Labelle et al. |
| 6,423,338 B1 | 7/2002 | Larson et al. |
| 2001/0007663 A1 | 7/2001 | Von Corswant |
| 2001/0046474 A1 | 11/2001 | Weers et al. |

FOREIGN PATENT DOCUMENTS

| | | |
|---|---|---|
| DE | 2 513 797 | 10/1975 |
| DE | 2 938 807 | 11/1980 |
| DE | 3 421 468 | 12/1985 |
| DE | 4 440 337 | 5/1996 |
| EP | 0 036 277 | 3/1981 |
| EP | 0 052 322 | 5/1982 |
| EP | 0 153 926 | 6/1984 |
| EP | 0 272 091 | 6/1988 |
| EP | 0 355 095 | 8/1988 |
| EP | 0 330 532 | 1/1989 |
| EP | 314 060 | 5/1989 |
| EP | 0 391 369 | 4/1990 |
| EP | 0 418 153 | 3/1991 |
| EP | 0 499 299 | 8/1992 |
| EP | 539 319 | 4/1993 |
| EP | 0 570 829 | 5/1993 |
| EP | 0 456 764 | 9/1993 |
| EP | 0 589 843 | 9/1993 |
| EP | 0 601 618 | 10/1993 |
| EP | 0 456 670 | 11/1993 |
| EP | 0 602 700 | 12/1993 |
| EP | 0 580 690 | 2/1994 |
| EP | 589 843 | 3/1994 |
| EP | 636 618 | 2/1995 |
| EP | 670 715 | 9/1995 |
| EP | 0 605 497 | 3/1996 |
| EP | 0 724 877 | 8/1996 |
| EP | 0 757 911 | 2/1997 |
| EP | 760 237 | 3/1997 |
| EP | 0 770 381 | 5/1997 |
| FR | 2 617 047 | 12/1988 |
| GB | 2 046 094 | 4/1980 |
| GB | 2 217 173 | 10/1989 |
| GB | 2 298 789 | 3/1995 |
| GB | 1 527 638 | 3/1996 |
| HU | 211 580 B | 6/1995 |
| JP | 56167616 | 5/1980 |
| JP | 1502590 | 11/1980 |
| JP | 55141407 | 11/1980 |
| JP | 60208910 | 11/1980 |
| JP | 63233915 | 10/1985 |
| JP | 63502117 | 9/1986 |
| JP | 5221852 A | 8/1993 |
| WO | WO 85/00011 | 1/1985 |
| WO | WO 87/04592 | 8/1987 |
| WO | WO 88/04924 | 7/1988 |

| | | |
|---|---|---|
| WO | WO 9104011 | 4/1991 |
| WO | WO 91/16068 | 10/1991 |
| WO | WO 92/18104 | 10/1992 |
| WO | WO 92/18105 | 10/1992 |
| WO | WO 93/05768 | 4/1993 |
| WO | WO 93/19736 | 10/1993 |
| WO | WO 94/08603 | 4/1994 |
| WO | WO 94/08605 | 4/1994 |
| WO | 94/12031 | 6/1994 |
| WO | WO 94/14415 | 7/1994 |
| WO | WO 94/20072 | 9/1994 |
| WO | WO 94/23733 | 10/1994 |
| WO | 94/26728 | 11/1994 |
| WO | WO 94/25068 | 11/1994 |
| WO | WO 94/26728 | 11/1994 |
| WO | WO 95/11039 | 4/1995 |
| WO | WO 96/01637 | 6/1995 |
| WO | WO 95/33490 | 12/1995 |
| WO | 96/02247 * | 2/1996 |
| WO | 96/02247 A1 | 2/1996 |
| WO | WO 96/13273 | 5/1996 |
| WO | WO 96/19064 | 6/1996 |
| WO | WO 96/21439 | 7/1996 |
| WO | WO 96/24332 | 8/1996 |
| WO | WO 96/29064 | 9/1996 |
| WO | 96/35415 * | 11/1996 |
| WO | WO 96/34515 * | 11/1996 |
| WO | WO 96/35415 | 11/1996 |
| WO | WO 97/00080 | 1/1997 |
| WO | WO 97/02042 | 1/1997 |
| WO | 97/10849 | 3/1997 |
| WO | WO 97/10814 | 3/1997 |
| WO | WO 97/12626 | 4/1997 |
| WO | WO 97/14407 | 4/1997 |
| WO | 97/15269 | 5/1997 |
| WO | WO 97/19692 | 6/1997 |
| WO | WO 97/22358 | 6/1997 |
| WO | WO 97/25977 | 7/1997 |
| WO | WO 97/26003 | 7/1997 |
| WO | 97/27855 | 8/1997 |
| WO | 97/33552 | 9/1997 |
| WO | WO 97/36610 | 10/1997 |
| WO | 97/48689 | 12/1997 |
| WO | 98/07434 | 2/1998 |
| WO | 98/30205 | 7/1998 |
| WO | WO 98/41239 | 9/1998 |
| WO | WO 98/53805 | 12/1998 |
| WO | WO 99/29300 | 6/1999 |
| WO | WO 99/29316 | 6/1999 |
| WO | WO 99/39696 | 8/1999 |
| WO | WO 99/49846 | 10/1999 |
| WO | WO 99/49848 | 10/1999 |
| WO | WO 00/10531 | 3/2000 |
| WO | WO 00/24376 | 5/2000 |
| WO | WO 00/40219 | 7/2000 |
| WO | WO 00/41682 | 7/2000 |
| WO | WO 00/54588 | 9/2000 |
| WO | WO 00/59471 | 10/2000 |
| WO | WO 00/59472 | 10/2000 |
| WO | WO 00/78301 | 12/2000 |
| WO | WO 01/30372 | 5/2001 |
| WO | WO 02/21517 | 3/2002 |

OTHER PUBLICATIONS

Windholz, M. The Merck Index Merck & Co., INC. 10th Edition Rahway, NJ Pp. 779-780 1983.*
"A Submicron Lipid Emulsion Coated With Amphipathic Polyethylene Glycol for Parenteral Administration of Paclitaxel (Taxol)", Dept. of Biochemistry and Pharmacy, Åbo Akademi University, Åbo, Finland, Apr. 19, 1996, pp. 16-21.
"Mechanism of Anaphylactoid Reactions: Improper Preperation of High-Dose Intravenous Cyclosporine Leads to Bolus Infusion of Cremophor EL and Cyclosporine", Chu et al, The Annals of Pharmacotherapy, Nov. 1997, vol. 31, pp. 1287-1291.
"Methods for Preventing Reactions Secondary to Cremophor EL", L. Michaud. Annals of Pharmacotherapy, vol. 31, No. 11, Nov. 1997, pp. 1402-1404.
[LSP4]La Fuma Polmery 1998 43 nr 2. 104-108, "The role of water-soluble polymers at the solid/liquid etc."
"Derived Diameters and Distribution Statistics," from an unknown web-site, 6 pages.
"Getting Started", Man 0106, Issue 1.0, (Jan. 1996), Malvern Instruments Ltd., England, pp. 7.1-7.7.
Bangham et al., "Diffusion of Univalent Ions Across the Lamellae of Swollen Phospholipids", J. Mol. Biol. (1965) 13, pp. 238-252.
Benz et al., "Electrical Capacity of Black Lipid Films and of Lipid Bilayers Made from Monolayers", Biochem. Biophys. Acta, (1975) vol. 394, pp. 323-334.
Bergmann, Ludwig, Der Ultraschall, 5 Aufl., (1949), Stuttgart, S. 551-564, 672f.
Bittman, Robert, "Sterol-Polyene Antibiotic Complexation: Probe of Membrane Structure," Lipids, vol. 13, No. 10, pp. 686-691 (1978).
Buchmuller et al., "Cryopel: Ein neus Verfahren zum Pelletieren und Frosten Biologischer Substrate," Gas Aktuell, 35, 1(989), pp. 10-13.
Calvor et al. Pharm. Dev. Tech., 3(3), 297-205, 1998, "Production of Microparticles by High Pressure etc."
Cherney, L.S., "Tetracaine Hydroiodide: A long Lasting Local Anesthetic Agent for the Relief of Postoperative Pain", Anesth. Analg. (1963) vol. 42, No. 4, pp. 477-481.
Chulia et al., Powder Technology and Pharmaceutical Processes, (1994), pp. 66-67.
Cudd et al., "Liposomes Injected Intravenously into Mice Associate with Liver Mitochondria, " Biochem. Biophys Acta, (1984) vol. 774, pp. 169-180.
Gennaro et al., "Sustained-Release Drug Therapy," Remington's Pharmaceutical Sciences, 17th Ed., (1985). p. 1645.
Goodman and Gillman's, "The Pharmacological Basis of Therapeutics," 7th Ed., MacMillan Publishing Co., New York (1985) Chap. 15, p. 312.
Gregoriadis, Gregory, "The Carrier Potential of Liposomes in Biology and Medicine" New Engl. J. Med., (1976) vol. 295, No. 13, pp. 704-710.
Guzman et al., 1088 J. Pharm. Sci. 82 (1993) No. 5 pp. 498-502 Formation and Characterization of Cyclosporine-Loaded Nanoparticles.
Haynes et al., "Metal-Ligand Interactions in Organic Chemistry and Biochemistry", B. Pullman and N. Goldblum (eds.), part 2, (1977), pp. 189-212.
Haynes et al., "Ultra-Long Duration Local Anesthesia Produced by Injection of Lecithin-coated Methoxyflurane Microdroplets", Anesthesiology (1985) vol. 63, No. 5, pp. 490-499.
Herbert A. Leiberman and Leon Lachman, Eds., Pharmaceutical Dosage Forms, Tablets, vol. 1, (1980), p. 13.
Huang et al., "Interaction of the N-terminus of Sterol Carrier Protein 2 with Membranes: Role of Membrane Curvature", Biochem. J, (1999) vol. 8, pp. 593-603.

Kirkpatrick et al., "Local Anesthetic Efficacy of Methoxyflurane Microdroplets in Man," *Anesthesiology* (1987) 67(3A): A254.

Lehninger Biochemistry, "The Molecular Basis of Cell Structure and Function", (1970) Chapter 10.

Lourenco et al., Int. J. of Pharm. 138 (1996), 1-12, "Steric stabilization of nanoparticles:size and surface properties".

Luckham Pestic, Sci., 1989, 25, 25-34, "The Physical Stability of Suspension Concentrates with Particular etc."

Mishra et al., "Scientifically Speaking: Novel Injectable Formulations of Water-Insoluble Drugs", *Controlled Release Newsletter*, vol. 17, Issue 2, (Jun. 2000), pp. 21-30.

Miyajima, Koichiro, "Role of Saccharides for the Freeze-Thawing and Freeze-Drying of Liposome", *Advanced Drug Delivery Review*, vol. 24, (1997), pp. 151-159.

Muller et al., "Nanosuspensions for the I.V. Administration of Poorly Soluble Drugs-Stability During Sterilization and Long-Term Storage", Dept. of Pharmaceutics, Biopharmaceutics and Biotechnology, The Free University of Berlin, Kelchstraβe 31, D-12169 Berlin, Germany.

Muller et al., Emulsions and Nanosuspension, Chap. 9 (1998) p. 163.

Napper, "Polymeric Stabilizations of Colloidal Dispersions", (1983).

Pace et al., "Novel Injectable Formulations of Insoluble Drugs", *Pharmaceutical Technology*, vol. 23, No. 3, (Mar. 1999), pp. 116-134.

Rompp's Chemie Lexikon, 2 Aufl., Bd. 1, (1950), Stichwort, "Emulsion".

Ross et al., "Aqueous Solutions of Surface-Active Solutes", *Collodial Systems and Interfaces*, © 1988, pp. 148-151.

Sande et al., "Antimicrobial Agents: Antifungal and Antiviral Agents", pp. 1219-1222.

Siekmann et al. Pharm. Pharmacol Lett (1994) 3:225-228 "Melt-homogenized Solid Lipid Nanparticles Stabilized by the Non-Ionic Sufactant Tyloxapol".

Website http://userpage.fu-berlin.de/~kayser/nanosuspensionen.htm.

Wu et al., "Pharmacokinetics of Methoxyflurane After Its Intra-Dermal Injection as Lecithin-Coated Microdroplets, "*Journal of Controlled Release*, (1989), vol. 9, pp. 1-12.

Zuidam et al. "Sterilization of Liposomes by Heat Treatment", Pharmaceutical Research, vol. 10, No. 11, 1993 p. 1591-1596.

Arduino, M. J. et al., "Microbial Growth and Endotoxin Production in the intravenous Anesthetic Propofol", Infection Control and Hospital Epidemiology, vol. 12, No. 9, Sep. 1991, pp. 535-539.

Attwood, David, "Microemulsions," Colloidal Drug Delivery Systems, © 1994, pp. 31-33.

Babl et al., "New Formulations of Propofol in an LCT/MCT Emulsion: Approach to Reduce Pain on Injection", Eur. Hosp. Pharmacy. Jan. 1995, vol. 1, No. 1, pp. 15-21.

Bennett et al., "Postoperative Infections Traced to Contamination of an Intravenous Anesthetic, Propofol", Natl. Ctr. for Infectious Diseases, vol. 333, No. 3, (1999) pp. 2-9.

Caims et al., "Tolerance of Mixed Lipid Emulsion in Neonates: Effect of Concentration", Archives of Disease in Childhood, (1996), vol. 75, p. F113-F116.

Collins-Gold et al., "Parenteral Emulsions for Drug Delivery," Advanced Drug Delivery Reviews, (1990) vol. 5, pp. 189-208.

Cox et al., "Influence of Different Fat Emulsion-Based Intravenous Formulations on the Pharmacokinetics and Pharmacodynamics of Propofol," Pharmaceutical Research, (1998) vol. 15, No. 3 pp. 442-448.

Crowther et al., "Growth of Microorganisms in Propofol, Thiopental and a 1:1 Mixture of Propofol and Thiopental", Anesth. Analg. (1996), vol. 82, pp. 475-478.

De Sommer et al., "A Comparative Study on the Effects Of Propofol in Emulsion and Intralipid® on Fat Metabolism," Acta Anesthesiologica Belgica, (1990) vol. 41, No. 2, pp. 133-138.

Dewandre et al., "A Comparison of the 2% and 1% Formulations of Propofol During Anaesthesia for Craniotomy," Anesthesia, (1994), vol. 49, pp. 8-12.

"Diprivan 1% Injection,"Physicians Desk Reference, 1999, pp. 3411-3418.

Doenicke, A.W. et al., "Pharmacokinetics and Pharmacodynamics of Propofol in a New Solvent", Anesth. Analg., (1997), vol. 85, pp. 1399-1403.

Doenicke, A.W. et al., "Reducing Pain During Propofol Injection: The Role of the Solvent", Anesth. Analg., (1996), vol. 82, pp. 472-474.

Eddleston et al., "The Effect on Serum Lipid Concentrations of a Prolonged Infusion of Propofol—Hypertriglyceridaemia Associated with Propofol Administration," Intensive Care Med., (1991), vol. 17, pp. 424-426.

Ewart et al., "Forum: 2% Propofol for Sedation in the Intensive Care Unit, A Feasibility Study", Anaesthesia, Feb. 1992, vol. 47, No. 2, pp. 146-148.

Freeman, Andrew B., "A Technique for Reducing Pain Associated with Propofol Administration,"Anesth. Analog., 1992 (1 page).

Ghouri et al., "Effect of Flumazenil on Recovery after Midazolam and Propofol Sedation", Anesthesiology, (1994), vol. 81, pp. 333-339.

Gottardis et al., Effect of Prolonged Sedation with Propofol on Serum Triglyceride and Cholesterol Concentrations, British J. Anaesthesia, (1989) vol. 62, pp. 393-396.

King et al., "Lidocaine for the Prevention of Pain Due to Injection of Propofol", Anesth. Analg. (1992), vol. 74, pp. 246-249.

Lindholm, Marianne, "Critically Ill Patients and Fat Emulsions," Minerva Anesthesiology, (1992), vol. 58, No. 10, pp. 875-879.

Mangar et al., "Tourniquet at 50 mm Hg Followed by Intravenous Lidocaine Diminishes Hand Pain Associated with Propofol Injection", Anesth, Analg., (1992), vol. 74, pp. 250-252.

Mirakhur et al., "Induction Characteristics of Propofol in Children: Comparison with Thiopentone", Anesthesia, (1998), vol. 43, pp. 593-598.

Nichols, Ronald Lee, "Bacterial Contamination of an Anesthetic Agent," New Engl. J. Med., (1995), vol. 333, No. 3, pp. 184-185.

Peereboom et al., "Successful Re-treatment with Taxol After Major Hypersensitivity Reactions", J. Clin. Oncology, vol. 11 No. 5, 1993, pp. 885-890.

Sandstrom et al., "Structured Triglycerides Were Well Tolerated and Induced Increased Whole Body Fat Oxidation Compared With Long-Chain Triglycerides in Postoperative Patients", Journal of Parenteral and Enteral Nutrition, (1995), vol. 19 No. 5, pp. 381-386.

Sharma et al., "Novel Taxol Formulations: Preperation and Taxation of Taxol-Containing Liposomes," Pharm. Res vol. 11 No. 6, 1994, pp. 889-896.

Sklar, Grant E., "Propofol and Postoperative Infections," The Annals of Pharmacotherapy, (1997), vol. 31, pp. 1521-1523.

Smith et al., "Propofol: An Update on its Clinical Use," Anesthesiology, Oct. 1994, vol. 81, No. 4, pp. 1005-1043.

Stark et al., "A review of the safety and tolerance of propofol ('Diprivan')", Postgraduate Medical Journal, 1985, vol. 61, Suppl. 3, pp. 152-156.

Stenz et al., "A new physiologically approached in vitro test for quick evaluation of the hemolytic activity of surfactants", Pharmazie, (1996), vol. 51, No. 5, pp. 283-287.

Sosis et al., "Propofol, but not Thiopental, Supports the Growth of Candida Albicans", Anesth. Anal., (1995), vol. 81, pp. 132-134.

Tarr et al., "A New Parenteral Emulsion for the Administration of Taxol," Pharmaceutical Research, vol. 2, No. 2, 1987, pp. 162-165.

Tessler et al., "Growth curves of Staphylococcus aureus, Candida, albicans, and Moraxella osioensis in propofol and other media", Can. J. Anaesth. (1992), vol. 39 No. 5, pp. 509-511.

White et al., "Sedative Infusions During Local and Regional Anesthesia: A Comparison of Midazolam and Propofol", J. Clin. Anesth., Jan./Feb. 1991, vol. 3, pp. 32-39.

Sosis, et al., Growth of *Staphylococcus aureus* in Four Intravenous Anesthetics, Anesth Analg (1993) vol. 77, pp. 766-768.

Groves, et al., "The self-emulsifying action of mixed surfactants in oil", Acta Pharm. Suecica, vol. 13, (1976), pp. 361-372.

Sharma, et al., "Novel Taxol® Formulation: Polyvinylpyrrolidone Nanoparticle-Encapsulated Taxol® for Drug Delivery in Cancer Therapy", Oncology Research, vol. 8, Nos. 7/8, pp. 281-286, (1996).

Wheeler, et al., "Polyethylene Glycol Modified Phospholipids Stabilize Emulsions Prepared from Triacylglycerol", J. of Pharmaceutical Sciences, vol. 83, No. 11, pp. 1558-1564, (Nov. 1994).

Lundberg, B., "Preparation of Drug-Carrier Emulsions Stabilized with Phosphatidylcholine-Surfactant Mixtures", J. of Pharmaceutical Sciences, vol. 83, No. 1, pp. 72-75, (1994).

Sjöström, et al., "A Method for the Preparation of Submicron . . . and Surfactant Concentration", J. of Pharmaceutical Sciences, vol. 82, No. 6, pp. 579-583, (Jun. 1993).

Benita, et al., "Submicron Emulsions as Colloidal Drug . . . Physicochemical Characterization", J. of Pharmaceutical Sciences, vol. 82, No. 11, pp. 1069-1079, (Nov. 1993).

Lundberg, B., "A Submicron Lipid Emulsion Coated with Amphipathic Polyethylene Glycol for Parenteral Administration of Paclitaxel (Taxol)", J. Pharm. Pharmacol., vol. 49, pp. 16-21, (1997).

Adams, et al., "Taxol: A History of Pharmaceutical Development and Current Pharmaceutical Concerns", J. of the Natl. Cancer Inst. Monographs, No. 15, pp. 141-147, (1993).

Terwogt, et al., "Alternative formulations of paclitaxel", Cancer Treatment Reviews, vol. 23, pp. 87-95, (1997).

Groves et al., "Rheological characterization of self-emulsifying oil/surfactant systems", Acta Pharm. Suecica, vol. 13, pp. 353-360, (1976).

Eugster, et al., "Marigenol®-Concentrates comprising Taxol and/or Taxan esters as active substances", Panminerva Med., vol. 38, pp. 234-242, (1996).

Gershanik, et al., "Positively Charged Self-Emulsifying Oil Formulation for Improving Oral Bioavailability of Progesterone", Pharm. Dev. Tech., vol. 1, No. 2, pp. 147-157, (1996).

Constantinides, P., "Lipid Microemulsions for . . . Biopharmaceutical Aspects", Pharm. Research, vol. 12, No. 11, pp. 1561-1572, (1995).

Sharma, et al., "Novel Taxol Formulations: Preparation and Characterization of Taxol-Containing Liposomes", Pharm. Research, vol. 11, No. 6, pp. 889-896, (1994).

Constantinides, P.,et al. "Formulation and Intestinal Absorption . . . Medium-Chain Glycerides", Pharm. Research, vol. 11, No. 10, pp. 1385-1390, (1994).

Kurihara, et al., "Enhanced Tumor Delivery and Antitumor Activity of Palmitoyl Rhizoxin Using Stable Lipid Emulsions in Mice", Pharm. Research, vol. 13, No. 2, pp. 305-310, (1996).

* cited by examiner

ANTICANCER COMPOSITIONS

Benefit of provisional application Ser. Nos. 60/080,272 and 60/080,273 both filed Apr. 1, 1998, the disclosures of which are hereby incorporated by reference, is claimed.

FIELD OF INVENTION

The present invention relates generally to cancer therapeutics. More particularly it is directed to novel pharmaceutical compositions of water insoluble anticancer drugs for therapeutic administration as exemplified by the taxanes which include paclitaxel, docetaxel and their derivatives and analogues.

BACKGROUND AND SUMMARY OF THE INVENTION

Paclitaxel is a taxane and a member of the terpenoid family of compounds present in very small quantities in the *Taxus brevifolia* species such as the pacific Yew tree. These compounds, collectively known as taxoids, taxins or taxanes, have potent anticancer properties in, among others, ovarian cancer, lymphoma, and breast cancer. Because of its poor solubility in water, the current commercial formulation of paclitaxel is prepared by dissolving 6 mg of the drug in one milliliter of a mixture of polyoxyethylated castor oil (Cremophor®(EL) and dehydrated alcohol. The commercially available paclitaxel formulation is for intravenous administration only. There exists no commercial formulation of paclitaxel, which can be administered orally. The commercial injectable formulation is physically unstable especially for treatments requiring long infusion time. The infusate may contain up to 10% each of alcohol and Cremophor®EL. The physical stability of the paclitaxel formulation may be increased by increasing the amounts of Cremophor®EL in the formulation, but may also lead to an increased incidence of adverse reactions. Yet another approach as described in U.S. Pat. No. 5,681,846 is to decrease the drug and Cremophor® concentration and increase the alcohol content in the formulation.

An undesirable effect of Cremophor®EL in paclitaxel and other drug formulations is the production of possible anaphylactoid reaction with associated dyspnea, hypotension, angioedema and uticaria. Cremophor®EL is also known to extract plasticizers such as di-ethylhexyl-phthalate from the polymers commonly used intravenous infusion tubings and infusion bags. These plasticizers are known to promote toxic reactions, such as Adult Respiratory Distress Syndrome (ARDS), in patients which have been exposed to high levels.

Various other methods have been used to increase the water solubility of paclitaxel and other anticancer drugs, for example, by conjugation of the water insoluble drug moiety with water soluble polymers as taught by U.S. Pat. No. 5,437,055, WO 97/10849, and WO 97/33552. While WO 94/12031 teaches that a composition of paclitaxel with Cremophor®EL, absolute alcohol and citric acid increases the stability however, no mention is made if the proposed composition increases the solubility of paclitaxel. Others have used liposome preparations as a means of eliminating Cremophor®EL and reducing vehicle toxicity as described by Sharma et al (Pharm. Res. 11:889–896, 1994). An oil-in-water emulsion (U.S. Pat. No. 5,616,330) is another approach to preparing Cremophor® free paclitaxel formulation. The latter two formulation approaches have limitations in terms of low degree of drug loading. Yet another approach uses cyclodextrins to make a water-soluble formulation of paclitaxel as described in WO 94/26728.

The present invention is based on a strong need for a safer and stable injectable and oral formulation of anticancer drugs, particularly the taxanes such as paclitaxel, docetaxel and their derivatives and analogues and other anticancer drugs.

U.S. Pat. No. 5,407,683 discloses a composition containing paclitaxel in squalene as solution in absence of a surfactant and then forming a self-emulsifying glass by addition of an aqueous sucrose solution followed by evaporation of water. The resulting glass upon mixing with water forms an emulsion with a particle size in a range of 2 to 10 $\mu$m. The preparation of such glass requires the use of undesirable organic solvents, which must be completely removed before medical use.

Quay et al describe a conventional oil-in-water emulsion system (WO 98/30205) consisting of vitamin E as a carrier oil in which a drug may be dissolved, together with polyethyleneglycol and related surfactants. Conventional emulsions have limited shelf life and are often difficult to terminally heat sterilize or even filter sterilize. The particle size of conventional emulsions is usually far greater than microemulsions.

Microemulsions are thermodynamically stable and optically transparent or opaque depending on the particle size of the emulsion. Microemulsions have a mean droplet size of less than 200 nm, in general between 20–100 nm. In contrast to conventional emulsions, the microemulsions are formed in the presence of an aqueous phase by self emulsification without any energy input. In the absence of water, this self emulsifying system exists as a transparent-looking mixture of oil and surfactants in which a lipophilic drug is dissolved.

Wheeler et al describe an emulsion preparation (U.S. Pat. No. 5,478,860) containing a mixture of paclitaxel, an oil and a polyethylene glycol-linked lipid which is covered by a monolayer of a polar lipid such as phosphatidylglycerol or phosphatidylethanolamine. This mixture, after homogenization in presence of an aqueous phase at appropriate pressure, yields an emulsion with a particle size in the range of 100 nm. It is not known if this is the mean or minimum particle size and if it is number weighted or volume weighted. The necessity of using undesirable organic solvents for initial dissolution of ingredients is not advisable even if the organic solvent is removed prior to use. In addition to an elaborate evaporation step, the method requires input of energy by way of high pressure homogenization adding to the overall cost. Because the preconcentrate of a true microemulsion is usually non-aqueous, it can provide longer shelf life than a regular emulsion which is in aqueous suspension.

Lacy et al disclose a capsule delivery system (U.S. Pat. No. 5,645,856) for oral delivery of hydrophobic drugs containing a digestible oil, and a combination of surfactants. The selection of surfactant is made such that it inhibits the in vivo lipolysis of the oil.

Eugster discloses an ultra microemulsion system (Swiss Patent CH 688 504 A5) for paclitaxel and its analogs composed of an oil and one or more surfactants providing a formulation of the drug with a mean particle size of 2.2–3 nm thus approaching a solution rather than an emulsion. It is not known if this formulation is useful for oral, injectable or topical use.

There have been attempts to enhance oral activity of taxanes by co-administration of taxanes with another drug such as cinchonine (WO 97/27855) or cyclosporin, ketoconazole etc. (WO 97/15269). Similarly, WO 97/48689 describes the use of various carbocyclic compounds in combination with anticancer drugs to enhance oral bioavailability of the drug. All three of these approaches have the drawback of combination drug therapy where a second drug with drastically different pharmacological activity is administered. In practice such a drug combination approach is the last resort taken by those familiar with the drug development process due to drastic increase in preclinical and clinical regulatory requirement for approval resulting in increasing cost and time to market.

SUMMARY OF THE INVENTION

In accordance with the present invention it has now surprisingly been found that particularly stable anticancer drug formulations, particularly the taxanes, that self emulsify in aqueous medium giving an average particle size in a range of about 10 nm to about 10 microns and that have improved bioavailability characteristics, are obtainable. Also described are self-emulsifying preconcentrates that disperse, without the input of high energy (i.e., other than mixing energy to cause dispersion), to form droplets of average size of up to about 10 microns.

Accordingly, this invention provides a pharmaceutical composition in the form of a self-emulsifying preconcentrate comprising an anticancer drug as the active ingredient solubilized in a carrier medium comprising at least one hydrophobic component, at least one hydrophilic component and at least one surfactant.

The self-emulsifying systems and their corresponding preconcentrates described in this invention consist of a hydrophobic component, an ingredient selected from triglycerides, diglycerides, monoglycerides, free fatty acids, and fatty acid esters (such as fatty acid esters of hydroxyalkanes or of dihydroxyalkanes) and derivatives thereof, individually or in combination. Preferably the surfactant is a non-ionic surfactant or a mixture of non-ionic surfactants. The invention is also characterized as optionally including a hydrophilic component, for instance a hydroxyalkane such as ethanol and/or a dihydroxyalkane such as 1,2-propylene glycol and/or a polyethylene glycol having an average molecular weight of less than or equal to 1000.

Compositions of the current invention will include, in addition to the water insoluble drug, the hydrophobic components and the optional hydrophilic components, and at least one surfactant. Examples of suitable surfactants are:

1. Polyoxyethylene-sorbitan-fatty acid esters; e.g. mono- and tri-lauryl, palmityl, stearyl and oleyl esters; e.g. products of the type known as polysorbates and commercially available under the trade name "Tween".
2. Polyoxyethylene fatty acid esters, e.g., polyoxyethylene stearic acid esters of the type known and commercially available under the trade name Myrj.
3. Polyoxyethylene castor oil derivatives, e.g., products of the type known and commercially available as Cremophors®. Particularly suitable are polyoxyl 35 castor oil (Cremophor® EL) and polyoxyl 40 hydrogenated castor oil (Cremophor® RH40).
4. α-tocopherol, α-tocopheryl polyethylene glycol succinate (vitamin E TPGS), α-tocopherol palmitate and α-tocopherol acetate.
5. PEG glyceryl fatty acid esters such as PEG-8 glyceryl caprylate/caprate (commercially known as Labrasol), PEG-4 glyceryl caprylate/caprate (Labrafac Hydro WL 1219), PEG-32 glyceryl laurate (Gelucire 44/14), PEG-6 glyceryl mono oleate (Labrafil M 1944 CS), PEG-6 glyceryl linoleate (Labrafil M 2125 CS).
6. Propylene glycol mono- and di-fatty acid esters, such as propylene glycol laurate, propylene glycol caprylate/caprate; also diethyleneglycol-monoethylether (DGME), commercially known as Transcutol (Gattefosse, Westwood, N.J.).
7. Sorbitan fatty acid esters, such as the type known and commercially available under the name Span (e.g., Span 20).
8. Polyoxyethylene-polyoxypropylene co-polymers, e.g., products of the type known and commercially available as Pluronic or Poloxamer.
9. Glycerol triacetate.
10. Monoglycerides and acetylated monoglycerides, e.g., glycerol monodicocoate (Imwitor 928), glycerol monocaprylate (Imwitor 308), and mono-and di-acetylated monoglycerides.

Suitable surfactants are not limited to those mentioned above, but may include any compound or compounds that would enhance the galenic properties of the preconcentrate.

Compositions in accordance with the present invention may include other ingredients in addition to the drug, one or more hydrophobic components, one or more hydrophilic components, one or more surfactants, inhibitors of cytochrome P450 enzymes or p-glycoprotein transport system such as grapefruit extract or compounds isolated from it. The composition may include, in addition to the forgoing, one or more ingredients, additives or diluents such as pharmaceutically acceptable polymeric or inorganic materials, antioxidants, preserving agents, flavoring or sweetening agents and so forth.

Compositions in accordance with the present invention may be liquid or solids at ambient temperature. They may be filled in soft or hard gelatin capsules in the form of liquid composition, molten composition, or granules or powder (if composition is solid at ambient temperature and was cooled and processed before filling). Coating may be also applied to capsules or tablets. The preconcentrate may be also be diluted with water to obtain stable emulsions that may be employed as drinking formulations, or packaged as such for injection after appropriate dilution with an aqueous medium, for example.

DETAILED DESCRIPTION OF THE INVENTION

A self-emulsifying preconcentrate of the present invention comprising an anticancer drug must contain a hydrophobic component, a surfactant and optionally a hydrophilic component. The surfactant and hydrophilic component are needed for the composition to form in aqueous medium a self-emulsifying system having an average particle size of between about 10 nm and about 10 microns. They may also help enhance the solubility and stability of the anticancer drug in the formulation. The hydrophobic component is needed because if it is not incorporated in appropriate amounts in the formulation, precipitation of the drug will be observed upon mixing of the composition with an aqueous medium and/or on storage. Similar observations may be made for the hydrophilic and surfactant components.

Based on the above, appropriate combinations or mixtures of a hydrophobic component, a surfactant and a hydrophilic component (when used) with the water insoluble drug are necessary to obtain a stable microemulsion preconcentrate that would yield upon mixing with an aqueous medium a stable dispersion with an average particle size of between about 10 nm and about 10 microns.

Preferred as hydrophobic components are triglycerides, diglycerides, monoglycerides, free fatty acids, and fatty acid esters and derivatives thereof, individually or in combination. Examples of hydrophobic components include but are not limited to propylene glycol dicaprylate/caprate, caprilic/capric triglyceride, caprylic/capric/linoleic triglyceride, e.g. synthetic medium chain triglycerides having C8–12 fatty acid chains or other derivatized (synthetic) triglycerides of the type known and commercially available under Miglyol 810, 812, 818, 829 and 840, linoleic acid, linoleic acid ethyl ester, fish oils as free fatty acids, their esterification and their transesterification products, e.g. of the type known and commercially available under EPAX 6000 FA, EPAX 4510 TG, individually or in combination. Additional examples include vegetable oils and C12–18 fatty acid mono-, di- and triglycerides prepared by individual admixing or as transesterification products of vegetable oils (such as soybean oil, almond oil, sunflower oil, olive oil or corn oil) with glycerol.

Preferred as hydrophilic components are 1,2-propylene glycol, ethanol and polyethylene glycol having an average molecular weight of less than or equal to 1000, individually or in combination. More preferred as hydrophilic components are 1,2-propylene glycol and ethanol, individually or in combination. Especially preferred as hydrophilic components is a combination or mixture of 1,2-propylene glycol and ethanol.

The relative proportion of the drug and the other ingredients in the composition of the current invention will vary depending whether it is delivered as a self-emulsifying preconcentrate or after dilution with water, depending on the particular ingredients and the desired physical properties of the formulation. Especially desired concentration limits in the self-emulsifying preconcentrate are as follows:

1. Oil phase: from 10 to 80% w/w of the preconcentrate. The oil phase may consist of triglycerides, diglycerides, monoglycerides, free fatty acids, propylene glycol mono or diesters and free fatty acids, esters and derivatives thereof, individually or in combination.
2. Cumulative amounts of surfactants: from 20 to 80% w/w of the preconcentrate.
3. Cumulative amounts of hydrophilic components, such as 1,2-propylene glycol and/or ethanol and/or a polyethylene glycol having an average molecular weight of less than or equal to 1000: from 0% to 40% w/w of the preconcentrate. The total of all ingredients will be 100%.

It is understood that the application of the teachings of the present invention, to the conditions described, will be evident to one skilled in the art of preparing such formulations, and to one skilled in treating such medical conditions. Additional features and advantages of the present invention are described below in preferred embodiments, which are intended as example, and not as limitation. In the following examples, the ingredients were weighed out into appropriate containers in the amounts described below. In all examples described below, a clear liquid was obtained upon appropriate mixing and heating.

EXAMPLES

The formulations represented in the following examples were prepared by mixing the oil components with surfactants and cosurfactants followed by the addition of drug powder as indicated. The composition may be prepared at room temperature or heated to 40–50° C. to accelerate the solubilization process. Several mixing techniques can be used ranging from mechanical stirring and agitation to sonication. All compositions shown below give liquid or semi-solid preconcentrates at room temperature.

An experiment to test the efficiency of forming microemulsions from the preconcentrates was carried out by diluting the preconcentrate in 20–50 fold with water or simulated gastric fluid with gentle mixing or shaking. The aqueous medium temperature varied between 20 and 37° C. Particle size analysis was then carried out using a photon correlation spectroscopy based particle sizer, Nicomp 370. Data reported in the following examples correspond to volume weighted particle size.

Example 1

| Ingredients | Amount (g) |
|---|---|
| Miglyol 840 | 1.971 |
| Cremophor ® RH40 | 2.190 |
| Imwitor 308 | 0.767 |
| Labrasol | 0.548 |
| Paclitaxel | 0.175 |
| Total | 5.651 |
| Mean particle size: | 31 nm |

Example 2

| Ingredients | Amount (g) |
|---|---|
| Miglyol 840 | 4.820 |
| Cremophor ® RH40 | 4.990 |
| Imwitor 308 | 1.750 |
| Labrasol | 1.250 |
| Paclitaxel | 0.489 |
| Transcutol | 2.000 |
| Total | 15.299 |
| Mean particle size: | 13 nm |

Example 3

| Ingredients | Amount (g) |
|---|---|
| Miglyol 840 | 1.396 |
| Cremophor ® RH40 | 1.551 |
| Imwitor 308 | 0.543 |
| Labrasol | 0.388 |
| Paclitaxel | 0.122 |
| Grapefruit extract | 0.400 |
| Total | 4.400 |
| Mean particle size: | 30 nm. |

Example 4

| Ingredients | Amount (g) |
|---|---|
| Miglyol 840 | 1.560 |
| Cremophor ® RH40 | 1.610 |

-continued

| Ingredients | Amount (g) |
|---|---|
| Imwitor 308 | 0.565 |
| Labrasol | 0.405 |
| Paclitaxel | 0.285 |
| Ethanol | 0.575 |
| Total | 5.000 |
| Mean particle size: | 14 nm |

Example 5

| Ingredients | Amount (g) |
|---|---|
| Miglyol 812 | 1.435 |
| Tween 80 | 2.150 |
| Lipoid E80 | 0.705 |
| Soybean oil | 0.178 |
| Linoleic acid | 0.174 |
| Ethanol | 0.305 |
| Paclitaxel | 0.068 |
| Total | 5.000 |
| Mean particle size: | 102 nm |

Example 6

Bioavailability of paclitaxel micro-emulsion preconcentrate was assessed using the formulation described in Example 1. Paclitaxel was given in doses of 2.5 mg/Kg or 5 mg/Kg to 8 male dogs of approximately 10 Kg body weight. The formulation was administered in the morning after overnight fasting in the form of a capsule followed by water. Free access to food and water was allowed two hours after dosing. Blood samples were drawn at different point (pre-dose, 0.5, 1, 2, 3, 4, 6, 8, 12, and 24 hr) and stabilized with EDTA, placed in Vacutainers, and stored at 2–8° C. The blood samples were then extracted using a liquid—liquid method and assayed by HPLC/UV. Bioavailability calculations were done by comparing the pharmacokinetic (PK) profiles obtained for orally given paclitaxel micro-emulsion preconcentrate with an intravenous commercial formulation. Bioavailability values ranging from 25% to 60% were obtained. FIG. 1 corresponds to a typical pharmacokinetic profile obtained for paclitaxel preconcentrate.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A storage-stable, self-emulsifying, and non-aqueous, preconcentrate of a taxane in a microemulsion comprising a taxane dissolved in a carrier system, which carrier system consists essentially of:
   10 to 80% w/w of a hydrophobic component selected from the group consisting of a triglyceride, a diglyceride, a monoglyceride, a free fatty acid, a fatty acid ester, a fish oil, a vegetable oil, and combinations thereof;
   20 to 80% w/w of a surfactant component consisting of one or more non-ionic surfactants;
   up to 35% w/w diethylene glycol monoethylether; and
   up to 40% w/w of a hydrophilic component selected from the group consisting of a hydroxyalkane, a dihydroxyalkane, a polyethylene glycol having an average molecular weight of at most 1000, and combinations thereof;
   wherein the preconcentrate, when mixed with water or simulated gastric fluid, forms a liquid having an average droplet size of at most 10 microns, and a dose of the preconcentrate has a taxane bioavailability of 25 to 60% of the taxane in the dose upon oral administration.

2. The self-emulsifying preconcentrate of claim 1, wherein the carrier system consists of 15 to 75% w/w of the hydrophobic component.

3. The self-emulsifying preconcentrate of claim 1, wherein the carrier system consists of up to 30% w/w of the hydrophilic component.

4. A storage-stable, self-emulsifying, and non-aqueous preconcentrate of at least one taxane in a composition consisting essentially of:
   10 to 80% w/w of a hydrophobic component selected from the group consisting of a triglyceride, a diglyceride, a monoglyceride, a free fatty acid, a fatty acid ester, a fish oil, a vegetable oil, and combinations thereof;
   20 to 80% w/w of a surfactant component consisting of one or more non-ionic surfactants; and
   up to 40% of a hydrophilic component selected from the group consisting of a hydroxyalkane, a dihydroxyalkane, a polyethylene glycol having an average molecular weight of at most 1000, 1,2-propylene glycol, ethanol, and combinations thereof;
   wherein the preconcentrate, when mixed with water or simulated gastric fluid, gives an average droplet size of at most 10 microns, and a dose of the preconcentrate has a taxane bioavailability of 25 to 60% of the taxane in the dose upon oral administration.

5. The preconcentrate of claim 4, wherein the hydrophilic component is selected from the group consisting of 1,2-propylene glycol and ethanol.

6. An orally administrable pharmaceutical composition consisting essentially of the preconcentrate of claim 4 in a pharmaceutically acceptable carrier or diluent.

7. A parenterally injectable pharmaceutical composition consisting essentially of the preconcentrate of claim 4 in a pharmaceutically acceptable diluent.

8. The preconcentrate of claim 4 filled in a soft or hard gelatin capsule.

9. The preconcentrate of claim 4, wherein the preconcentrate also includes an inhibitor of P-glycoprotein transport system or an inhibitor of cytochrome P450 enzyme.

10. The preconcentrate of claim 4, wherein the preconcentrate comprises grapefruit extract or a component thereof.

11. The preconcentrate of claim 4, wherein the taxane is paclitaxel or docetaxel.

12. A method of orally or parenterally administering a taxane to a subject in need of same comprising administering a dose of a storage-stable, self-emulsifying, emulsifying and non-aqueous preconcentrate of a taxane consisting essentially of:
   10 to 80% w/w of a hydrophobic component selected from the group consisting of a triglyceride, a diglyceride, a monoglyceride, a free fatty acid, a fatty acid ester, a fish oil, a vegetable oil, and combinations thereof;

20 to 80% w/w of a surfactant component consisting of one or more non-ionic surfactants; and up to 40% w/w of a hydrophilic component selected from the group consisting of a hydroxyalkane, a dihydroxyalkane, a polyethylene glycol having an average molecular weight of at most 1000, and combinations thereof;

wherein the preconcentrate, when mixed with water or simulated gastric fluid, gives an average droplet size of at most 10 microns, and a dose of the preconcentrate has a taxane bioavailability of 25 to 60% of the taxane in the dose upon oral administration.

13. The method of claim 12, wherein the taxane is solubilized in the preconcentrate.

14. A storage-stable, self-emulsifying, and non-aqueous preconcentrate; of a taxane in a microemulsion comprising a taxane dissolved in a carrier system, which carrier system consists essentially of:
10 to 80% w/w of a hydrophobic component;
20 to 80% w/w of a surfactant component consisting of one or more non-ionic surfactants; and
up to 40% w/w of a hydrophilic component.

15. The preconcentrate of claim 14, wherein the preconcentrate forms a liquid having an average droplet size of at most 10 microns when mixed with water or simulated gastric fluid.

16. The preconcentrate of claim 15, wherein a dose of the preconcentrate has a taxane bioavailability of 25 to 60% upon oral administration.

17. The preconcentrate of claim 16, wherein at least a portion of the hydrophilic component consists of ethanol, such that the carrier system contains at least 6% w/w ethanol.

18. The preconcentrate of claim 14, wherein the preconcentrate, when mixed with an aqueous medium and heated to 20–37° C., forms a liquid having an average droplet size of at most 10 microns.

19. The preconcentrate of claim 18, wherein the preconcentrate, upon oral administration, forms a microemulsion in situ in the gastrointestinal tract.

20. A storage-stable, self-emulsifying, and non-aqueous preconcentrate of a taxane in a microemulsion comprising a taxane dissolved in a carrier system, which carrier system consists essentially of:
10 to 80% w/w of a hydrophobic component;
20 to 80% w/w of a surfactant component; and
6% to 40% w/w of a hydrophilic component, at least a portion of which hydrophilic component consists of ethanol, such that the carrier system contains at least 6% w/w ethanol.

21. The preconcentrate of claim 20, wherein the surfactant component consists of one or more surfactants selected from the group consisting of polyoxyethylene-sorbitan-fatty acid esters, polyoxyethylene fatty acid esters, α-tocopherol, α-tocopheryl polyethylene glycol succinate, α-tocopherol palmitate, α-tocopherol acetate, PEG glyceryl fatty acid esters, propylene glycol mono- or di-fatty acid esters, sorbitan fatty acid esters, polyoxyethylene-polyoxypropylene co-polymers, glycerol triacetate, monoglycerides, and acetylated monoglycerides.

22. The preconcentrate of claim 21, wherein the preconcentrate forms a liquid having an average droplet size of at most 10 microns when mixed with water or simulated gastric fluid.

23. The preconcentrate of claim 22, wherein a dose of the preconcentrate has a taxane bioavailability of 25 to 60% upon oral administration.

24. The preconcentrate of claim 20, wherein the preconcentrate, when mixed with an aqueous medium and heated to 20–37° C., forms a clear liquid having an average droplet size of at most 10 microns.

25. The preconcentrate of claim 24, wherein the preconcentrate, upon oral administration, forms a microemulsion in situ in the gastrointestinal tract.

26. A storage-stable, self-emulsifying, and non-aqueous preconcentrate of a taxane in a microemulsion comprising a taxane dissolved in a carrier system, which carrier system consists essentially of:

10 to 80% w/w of a hydrophobic component selected from the group consisting of a triglyceride, a diglyceride, a monoglyceride, a free fatty acid, a fatty acid ester, a fish oil, a vegetable oil, and combinations thereof;

20 to 80% w/w of a surfactant component consisting of one or more surfactants selected from the group consisting of a polyoxyethylene-sorbitan-fatty acid ester, a polyoxyethylene fatty acid ester, a polyoxyethylene castor oil derivative, α-tocopherol, α-tocopheryl polyethylene glycol succinate, α-tocopherol palmitate, α-tocopherol acetate, a PEG glyceryl fatty acid ester, a propylene glycol mono- or di-fatty acid ester, a sorbitan fatty acid ester, a polyoxyethylene-polyoxypropylene co-polymer, glycerol triacetate, a monoglyceride, an acetylated monoglyceride, and combinations of any thereof; and 6% to 40% of a hydrophilic component, at least a portion of the hydrophilic component consisting of ethanol, such that the carrier system contains at least 6% w/w ethanol.

27. The preconcentrate of claim 26, wherein a dose of the preconcentrate has a taxane bioavailability of 25 to 60% upon oral administration.

28. An injectable pharmaceutically acceptable composition consisting essentially of a storage-stable, self-emulsifying, and non-aqueous preconcentrate of at least one taxane in a composition consisting essentially of:

10 to 80% w/w of a hydrophobic component;
20 to 80% w/w of a surfactant component; and
6% to 40% w/w of a hydrophilic component,
wherein (a) at least a portion of which hydrophilic component consists of ethanol, such that the composition contains at least 6% w/w ethanol, (b) the surfactant component of the composition consists of one or more non-ionic surfactants, or (c) conditions (a) and (b) apply.

29. A storage-stable, self-emulsifying, and non-aqueous, preconcentrate of a taxane in a microemulsion consisting of a taxane dissolved in a carrier system, which carrier system consists of:

10 to 80% w/w of a hydrophobic component selected from the group consisting of a triglyceride, a diglyceride, a monoglyceride, a free fatty acid, a fatty acid ester, a fish oil, a vegetable oil, and combinations thereof;

20 to 80% w/w of a surfactant component consisting of one or more non-ionic surfactants;

up to 35% w/w diethylene glycol monoethylether; and up to 40% w/w of a hydrophilic component selected from the group consisting of a hydroxyalkane, a dihydroxyalkane, a polyethylene glycol having an average molecular weight of at most 1000, and combinations thereof;

wherein the preconcentrate, when mixed with water or simulated gastric fluid, forms a liquid having an average droplet size of at most 10 microns, and a dose of the preconcentrate has a taxane bioavailability of 25 to 60% of the taxane in the dose upon oral administration.

30. A storage-stable, self-emulsifying, and non-aqueous preconcentrate of at least one taxane in a composition consisting of:

10 to 80% w/w of a hydrophobic component selected from the group consisting of a triglyceride, a diglyceride, a monoglyceride, a free fatty acid, a fatty acid ester, a fish oil, a vegetable oil, and combinations thereof;

20 to 80% w/w of a surfactant component consisting of one or more non-ionic surfactants; and up to 40% of a hydrophilic component selected from the group consisting of a hydroxyalkane, a dihydroxyalkane, a polyethylene glycol having an average molecular weight of at most 1000, 1,2-propylene glycol, ethanol, and combinations thereof;

wherein the preconcentrate, when mixed with water or simulated gastric fluid, gives an average droplet size of at most 10 microns, and a dose of the preconcentrate has a taxane bioavailability of 25 to 60% of the taxane in the dose upon oral administration.

31. A method of orally or parenterally administering a taxane to a subject in need of same consisting of administering a dose of a storage-stable, self-emulsifying, and non-aqueous preconcentrate of a taxane consisting of:

10 to 80% w/w of a hydrophobic component selected from the group consisting of a triglyceride, a diglyceride, a monoglyceride, a free fatty acid, a fatty acid ester, a fish oil, a vegetable oil, and combinations thereof;

20 to 80% w/w of a surfactant component consisting of one or more non-ionic surfactants; and up to 40% w/w of a hydrophilic component selected from the group consisting of a hydroxyalkane, a dihydroxyalkane, a polyethylene glycol having an average molecular weight of at most 1000, and combinations thereof;

wherein the preconcentrate, when mixed with water or simulated gastric fluid, gives an average droplet size of at most 10 microns, and a dose of the preconcentrate has a taxane bioavailability of 25 to 60% of the taxane in the dose upon oral administration.

32. A storage-stable, self-emulsifying, and non-aqueous preconcentrate of a taxane in a microemulsion consisting of a taxane dissolved in a carrier system, which carrier system consists of:

10 to 80% w/w of a hydrophobic component;

20 to 80% w/w of a surfactant component consisting of one or more non-ionic surfactants; and up to 40% w/w of a hydrophilic component.

33. The preconcentrate of claim 4, wherein the taxane is paclitaxel and is present in an amount of from 1.36% to 5.7% by weight of the preconcentrate.

34. The preconcentrate of claim 4, wherein the composition consists of 15 to 75% w/w of the hydrophobic component.

35. The preconcentrate of claim 4, wherein the hydrophobic component consists of a medium chain triglyceride.

36. The preconcentrate of claim 4, wherein the hydrophobic component consists of propylene glycol dicaprylate/caprate and is present in an amount of from 31.2 to 34.9% by weight of the preconcentrate.

37. The preconcentrate of claim 4, wherein the surfactant component consists of polyoxyl 40 hydrogenated castor oil, PEG-8 glyceryl caprylate/caprate, and glycerol monocaprylate.

38. The preconcentrate of claim 37, wherein the polyoxyl 40 hydrogenated castor oil is present in an amount of from 32.2 to 38.8% by weight of the preconcentrate.

39. The preconcentrate of claim 37, wherein the PEG-8 glyceryl caprylate/caprate is present in an amount of from 8.1 to 9.7% by weight of the preconcentrate.

40. The preconcentrate of claim 37, wherein the glycerol monocaprylate is present in amount of from 11.3 to 13.6% by weight of the preconcentrate.

41. The preconcentrate of claim 4, wherein the hydrophobic component consists of caprylic/capric triglyceride.

42. The preconcentrate of claim 41, wherein the caprylic/capric triglyceride is present in an amount of 28.7% by weight of the preconcentrate.

43. The preconcentrate of claim 1, wherein the taxane is docetaxel.

44. The method of claim 12, wherein the taxane is docetaxel.

45. The preconcentrate of claim 14, wherein the taxane is docetaxel.

46. The preconcentrate of claim 20, wherein the taxane is docetaxel.

47. The preconcentrate of claim 26, wherein the taxane is docetaxel.

48. The composition of claim 28, wherein the taxane is docetaxel.

49. The preconcentrate of claim 29, wherein the taxane is docetaxel.

50. The preconcentrate of claim 30, wherein the taxane is docetaxel.

51. The method of claim 31, wherein the taxane is docetaxel.

52. The preconcentrate of claim 32, wherein the taxane is docetaxel.

* * * * *

UNITED STATES PATENT AND TRADEMARK OFFICE
CERTIFICATE OF CORRECTION

PATENT NO. : 6,979,456 B1
APPLICATION NO. : 09/281430
DATED : December 27, 2005
INVENTOR(S) : Indu Parikh, Iskandar Moussa and Alain Carrier It is certified that error appears in the above-identified patent and that said Letters Patent is hereby corrected as shown below:

In Claim 40, Column 12, Lines 27-29 "The preconcentrate of claim 37, wherein the glycerol monocaprylate is present in amount of from 11.3 to 13.6% by weight of the preconcentrate." should read --The preconcentrate of claim 37, wherein the glycerol monocaprylate is present in an amount of from 11.3 to 13.6% by weight of the preconcentrate.--

Signed and Sealed this

Twenty-ninth Day of April, 2008

JON W. DUDAS
*Director of the United States Patent and Trademark Office*